(12) United States Patent
Lahiri et al.

(10) Patent No.: US 9,000,193 B2
(45) Date of Patent: Apr. 7, 2015

(54) PROCESS FOR THE PREPARATION OF CABAZITAXEL

(71) Applicant: Fresenius Kabi Oncology Limited, New Delhi (IN)

(72) Inventors: Saswata Lahiri, Gurgaon (IN); Nitin Gupta, Gurgaon (IN); Abul Azim, Gurgaon (IN); Nilendu Panda, Gurgaon (IN); Bhuwan Bhaskar Mishra, Gurgaon (IN); Sunil Sanghani, Gurgaon (IN)

(73) Assignee: Fresenius Kabi Oncology Limited, New Delhi (IN)

( * ) Notice: Subject to any disclaimer, the term of this patent is extended or adjusted under 35 U.S.C. 154(b) by 0 days.

(21) Appl. No.: 14/533,412

(22) Filed: Nov. 5, 2014

(65) Prior Publication Data

US 2015/0057454 A1 Feb. 26, 2015

Related U.S. Application Data

(62) Division of application No. 13/625,155, filed on Sep. 24, 2012, now Pat. No. 8,901,327.

(30) Foreign Application Priority Data

Sep. 26, 2011 (IN) .......................... 2794/DEL/2011

(51) Int. Cl.
C07D 305/14 (2006.01)
C07F 7/18 (2006.01)

(52) U.S. Cl.
CPC .................................. *C07F 7/1856* (2013.01)

(58) Field of Classification Search
USPC .................................................. 549/214, 510
See application file for complete search history.

(56) References Cited

U.S. PATENT DOCUMENTS

2001/0051736 A1 12/2001 Bouchard et al.
2012/0149925 A1 6/2012 Kung et al.

FOREIGN PATENT DOCUMENTS

| WO | 2009/115655 | 9/2009 |
| WO | 2012/088391 | 6/2012 |
| WO | 2012/142117 | 10/2012 |

OTHER PUBLICATIONS

Chen, "First Syntheses of C-4 Methyl Ether Paclitaxel Analogs and the Unexpected Reactivity of 4-Deacetyl-4-Methyl Ether Baccatin III," Tetrahedron Letters, vol. 37, No. 23, pp. 3935-3938 (1996).
Guillory, "Generation of Polymorphs, Hydrates, Solvates, and Amorphous Solids," Polymorphism in Pharmaceutical Solids, Jan. 1, 1999, pp. 183-226.
Nandakumar et al., "Mechanism of Solid Particle Degradation by *Aspergillus niger* in Solid State Fermentation," Process Biochemistry, vol. 29, Jan. 1, 1994, pp. 545-551.

*Primary Examiner* — Kristin Vajda
(74) *Attorney, Agent, or Firm* — Occhiuti & Rohlicek LLP

(57) ABSTRACT

The present invention discloses a process for the preparation of 4-acetoxy-2α-benzoyloxy-5β,20-epoxy-1-hydroxy-7β,10β-dimethoxy-9-oxotax-11-en-13α-yl(2R,3S)-3-tert-butoxycarbonylamino-2-hydroxy-3-phenyl-propionate Cabazitaxel (I).

2 Claims, 3 Drawing Sheets

PROCESS FOR THE PREPARATION OF CABAZITAXEL

CROSS-REFERENCE TO RELATED APPLICATIONS

Figure 1:
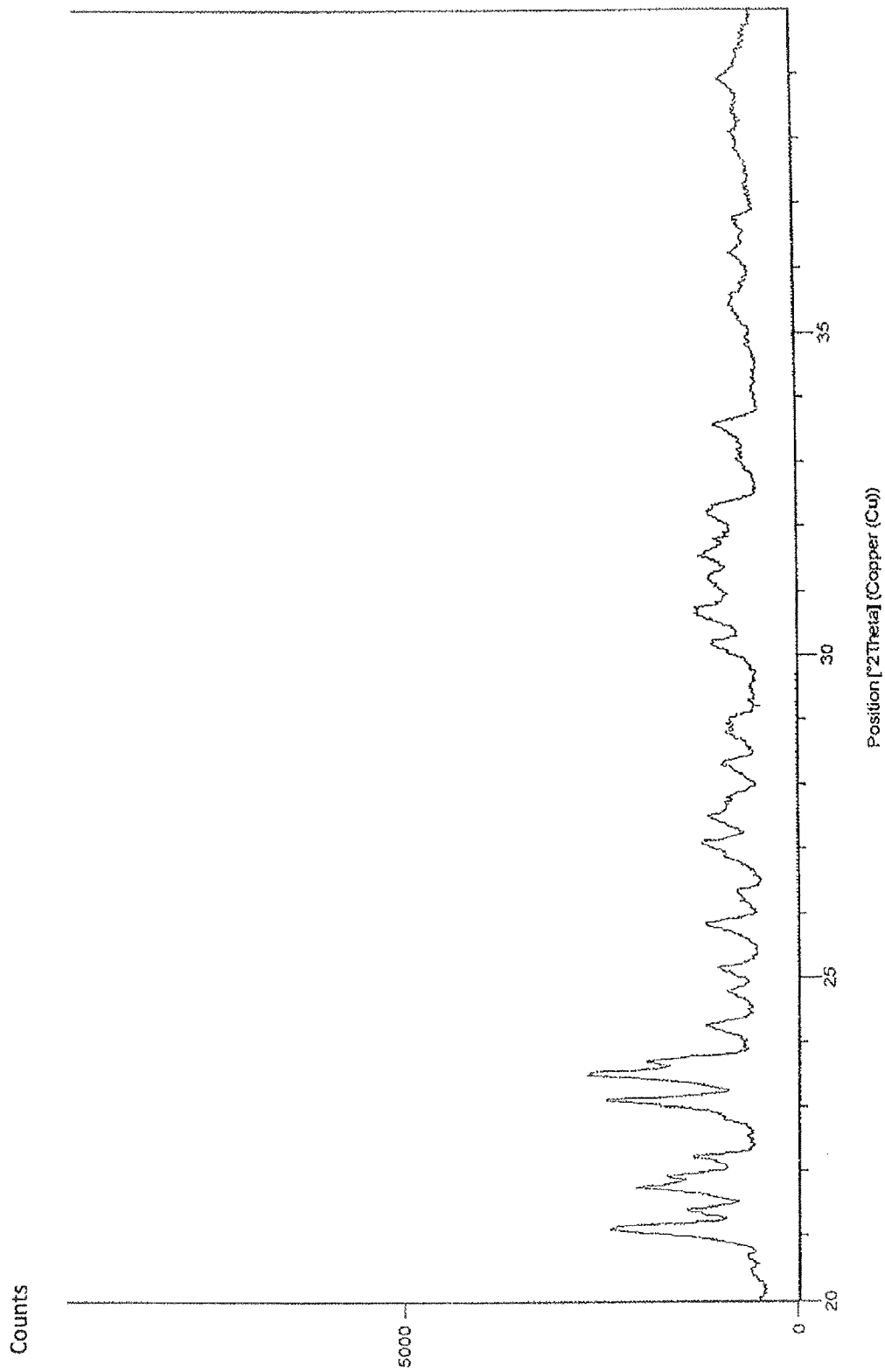

This application is a divisional of U.S. patent application Ser. No. 13/625,155, filed Sep. 24, 2012, which claims the benefit of the priority date of Indian Patent Application No. 2794/DEL/2011 filed Sep. 26, 2011. The contents of the aforementioned applications are hereby incorporated by reference in their entirety.

FIELD OF INVENTION

The present invention relates to an improved process for the preparation of Cabazitaxel and its Intermediates, with better yield and purity, which avoids the use of hazardous reagents.

BACKGROUND OF THE INVENTION

Cabazitaxel, which is chemically known as 4-acetoxy-2α-benzoyloxy-5β,20-epoxy-1-hydroxy-7β,10β-dimethoxy-9-oxotax-11-en-13α-yl(2R,3S)-3-tert-butoxycarbonylamino-2-hydroxy-3-phenyl-propionate is represented by Formula (I).

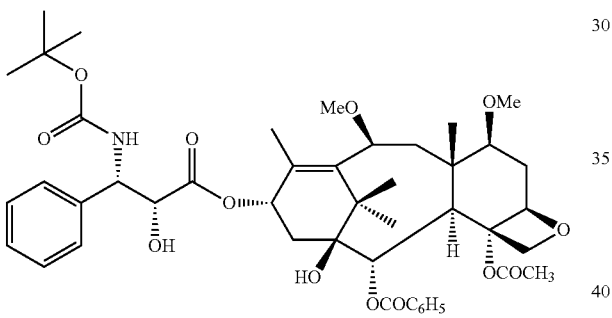

(I)

Cabazitaxel is a microtubule inhibitor indicated in combination with prednisone for treatment of patients with hormone-refractory metastatic prostate cancer previously treated with a docetaxel-containing treatment regimen, under the trade name Jevtana®.

U.S. Pat. No. 5,847,170 discloses the synthesis of Cabazitaxel by using 10-deacetyl baccatin III. The synthesis of Cabazitaxel as disclosed in U.S. Pat. No. 5,847,170 is summarized in Scheme-I Scheme-I Synthesis of Cabazitaxel as disclosed in U.S. Pat. No. 5,847,170

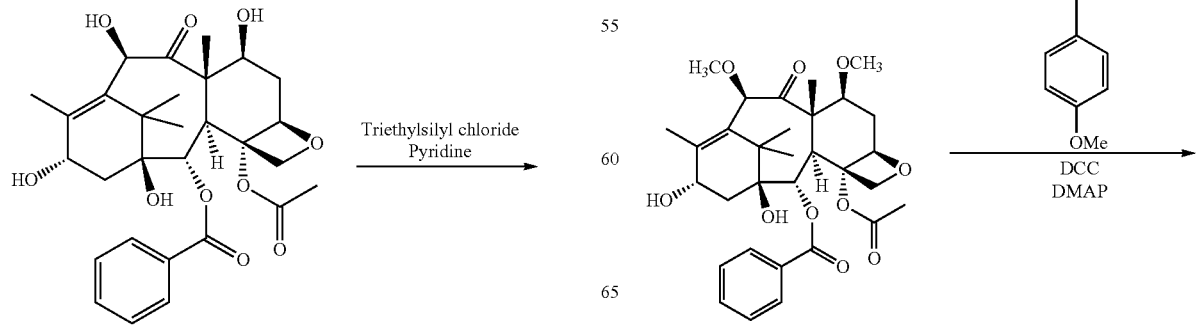

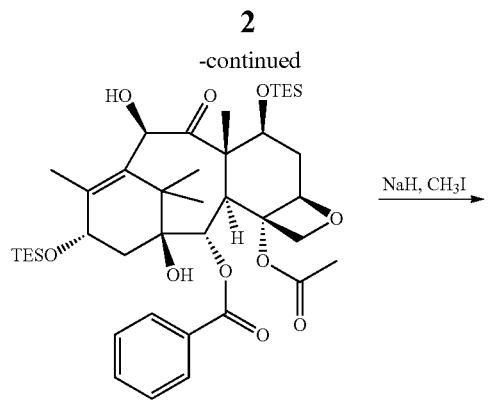

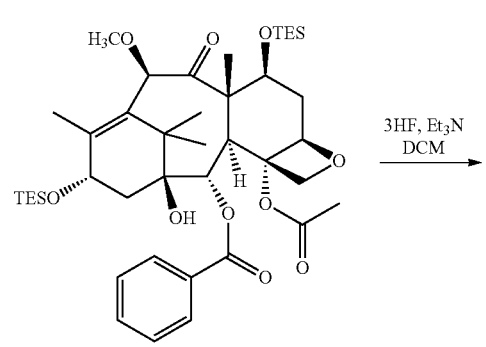

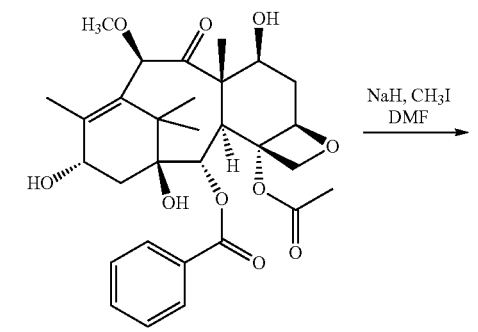

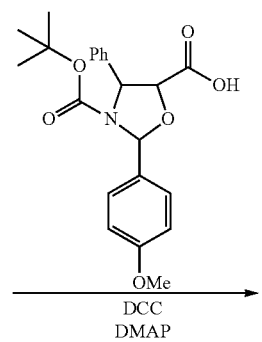

-continued

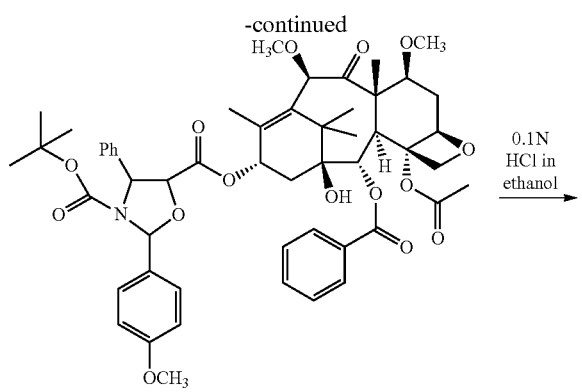

The major disadvantage of the process disclosed in U.S. Pat. No. 5,847,170 is that during the silylation of 10-DAB by using trimetheyl silyl chloride in Pyridine, several side products are being formed and silylated product is obtained in only 40-50% of yield.

The current process avoids the use of hazardous reagents, like Pyridine in the silylation step and hydrogen fluoride triethylamine complex (3HF.Et$_3$N) in the deprotection step.

The current process also utilizes the stochiometric quantity of methyl iodide for methylation in comparison to much higher quantities of the methyl iodide being used in the process described in U.S. Pat. No. 5,847,170, where in the example 1, methyl iodide is used as a solvent.

U.S. Pat. No. 5,962,705 discloses the synthesis of the intermediate of the Cabazitaxel having the Formula (II)

(II)

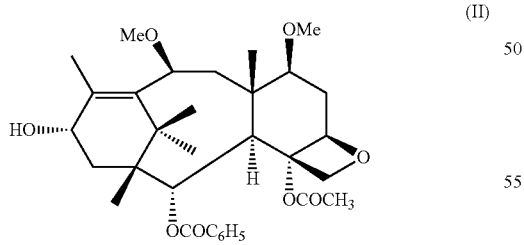

Several patents disclose the silylation of 10-DAB by using triethylsilyl chloride and Imidazole such as those described in U.S. Pat. No. 6,410,757, U.S. Pat. No. 6,500,858, U.S. Pat. No. 6,727,369 and U.S. Pat. No. 7,186,851, which are herein incorporated for reference only.

Tetrahedron Letters, Vol. 35, pp. 5543-5546, 1994 discloses the silylation at C-7 position by using triethyl silyl chloride and Imidazole in Dimethylformamide.

U.S. Pat. No. 5,962,705 discloses the methylation by using methyl iodide or methyl sulphate in the presence of an anionization agent such as one or more strong bases in anhydrous medium.

SUMMARY OF THE INVENTION

The first aspect of the present invention provides a first process for the preparation of Cabazitaxel of Formula (I)

(I)

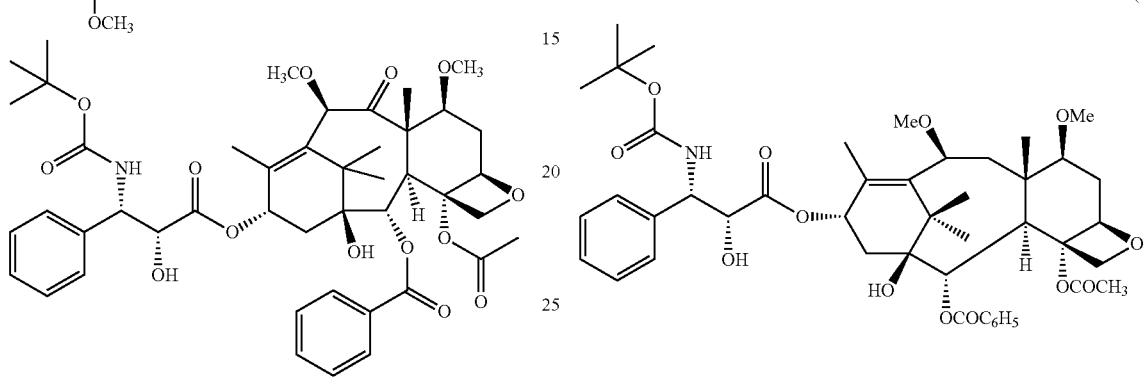

Comprising of:

a) Treating 10-deacetylbaccatin of Formula (III)

(III)

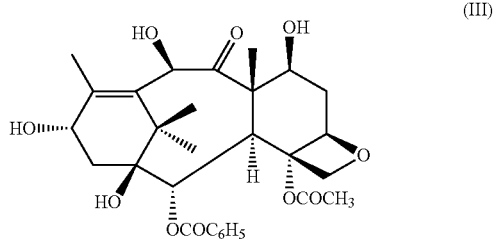

with a silylating agent in the presence of a base and a suitable organic solvent for 1-10 hours to obtain a compound of the Formula (IV)

(IV)

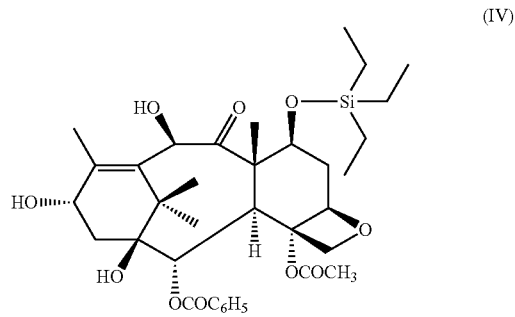

b) Methylating the compound of Formula (IV) in the presence of a base and a methylating agent to obtain a compound of Formula (V).

(V)

c) Deprotecting the silyl group of compound of Formula (V) in the presence of a suitable organic solvent and a base to obtain the compound of Formula (VI).

(VI)

d) Methylating the compound of Formula (VI) to give a compound of Formula (II) in the presence of a suitable organic solvent and a base.

(II)

e) Esterifying the compound of Formula (II) at C-13 Position by means of an acid or salt of Formula (VII), (VII)

wherein $R_1$ represents a benzoyl radical or a radical $R_2$—O—CO— in which $R_2$ represents a branched or unbranched alkyl, alkenyl, alkynyl, cycloalkyl, cycloalkenyl, bicycloalkyl, phenyl, tertiary butyl or nitrogenous heterocyclic radical, $R_3$ and $R_4$ are same or different and represent hydrogen, alkyl, alkoxyl or optionally substituted aryl and Ar represents an aryl radical, preferably a phenyl to obtain a product of general formula (VIII)

(VIII)

Deprotecting the side chain of the said product of formula (VIII) to obtain compound of Formula (IX), wherein $R_1$ and Ar are defined as above.

(IX)

g) Optionally converting compound of Formula (IX) to Cabazitaxel (I).

It is a preferred embodiment of the invention wherein the aryl rest Ar is a phenyl rest Ph, and R1 is a tert-Butyloxycarbonyl-rest (tBOC). In that embodiment there is no need to perform a step g), because Formula IX represents Cabazitaxel in that case.

If the Ar— differs from Ph- and/or R1- differs from tBOC- then the optional step g) in process 1 is performed to convert the compound of Formula IX into Cabazitaxel.

The second aspect of the present invention provides a second process for preparation of Cabazitaxel of Formula (I) comprising:

a) treating 10-deacetylbaccatin of Formula (III)

(III)

with silylating agent in the presence of base and a suitable organic solvent for 15-20 hrs to obtain a compound of the Formula (X)

e) deprotecting the silyl group of C-13 position of compound of Formula XIII to obtain the compound of Formula (II) in the presence of a suitable organic solvent and a base.

(X)

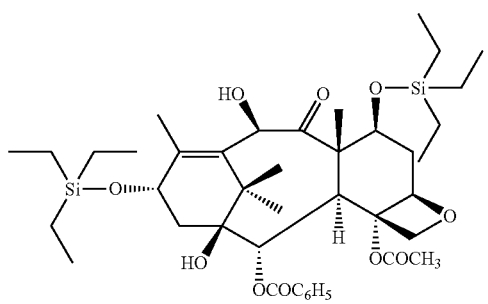

b) methylating the compound of formula (X) to obtain a compound of formula (XI) in the presence of a suitable organic solvent and a base;

(XI)

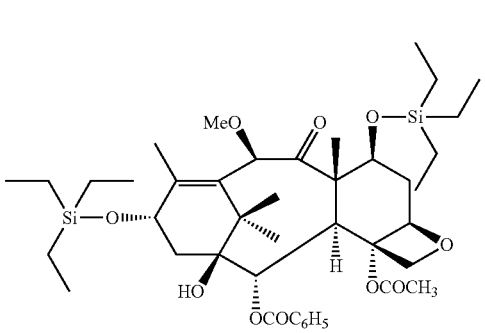

c) deprotecting the silyl group of compound of Formula XI to obtain the compound of Formula (XII) in the presence of suitable organic solvent and a base;

(XII)

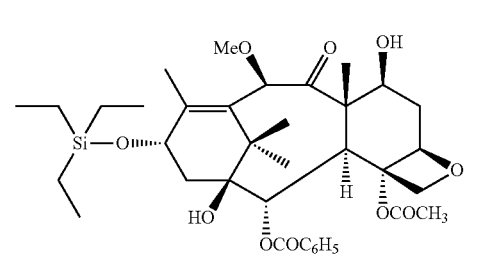

d) methylating the compound of Formula (XII to give a compound of Formula (XIII) in the presence of a suitable organic solvent and a base;

(XIII)

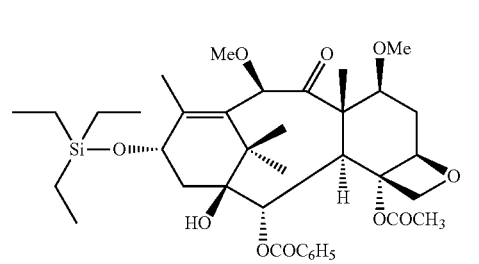

(II)

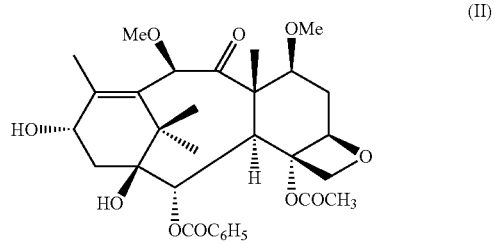

f) esterifying the compound of Formula (II) at C-13 Position by means of an acid or salt of Formula (VII), (VII)

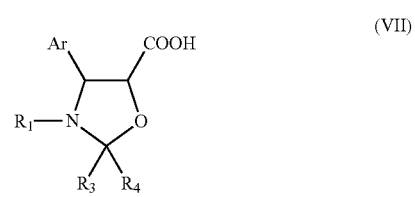

wherein $R_1$ represents a benzoyl radical or a radical $R_2$—O—CO— in which $R_2$ represents a branched or unbranched alkyl, alkenyl, alkynyl, cycloalkyl, cycloalkenyl, bicycloalkyl, phenyl, tertiary butyl or nitrogenous heterocyclic radical, R3 and R4 are same or different and represents is hydrogen, alkyl, alkoxyl or optionally substituted aryl and Ar represents an aryl radical preferably a phenyl to obtain a product of general formula (VIII);

(VIII)

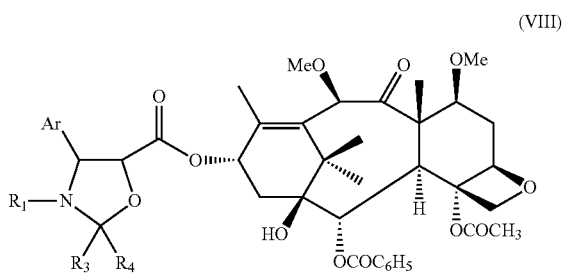

g) deprotecting the side chain of the said product of formula (VIII) to obtain compound of Formula (IX), wherein $R_1$ and Ar are as defined above; and (IX)

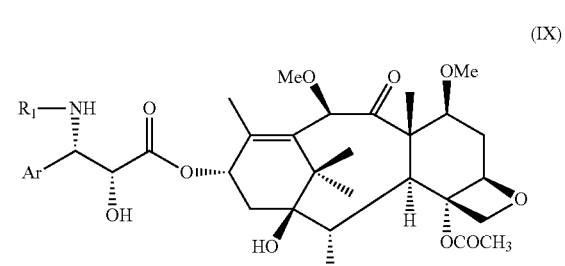

h) Optionally converting compound of Formula (IX) to Cabazitaxel (I).

It is preferred that the deprotecting step c) is performed selectively such that the majority of the product comprises one protective silyl group at C13-OH but not at C7-OH.

It is a preferred embodiment wherein the aryl substituent Ar— is a phenyl substituent Ph-, and the $R_1$ substituent is a tert butoxy-carbonyl-substituent (tBOC-). As such, it is a preferred embodiment of the invention wherein the final product of synthesis is Cabazitaxel, also known as (1S,2S,3R, 4S,7R,9S,10S,12R,15S)-4-(Acetyloxy)-15-{[(2R,3S)-3-[(tert-butoxy)carbonyl]amino}-2-hydroxy-3-phenylpropanoyl]oxy-1-hydroxy-9,12-dimethoxy-10,14,17,17-tetramethyl-11-oxo-6-oxatetracyclo[11.3.1.03,10.04,7]heptadec-13-en-2-ylbenzoat. In that embodiment there is no need to perform a step g), because Formula IX represents Cabazitaxel in that case.

If Ar— differs from Ph- and/or R1- differs from tBOC- then the optional step h) in process 2 is performed to convert the compound of Formula IX into Cabazitaxel.

The third aspect of the present invention relates to a novel intermediate of compound of Formula (XII)

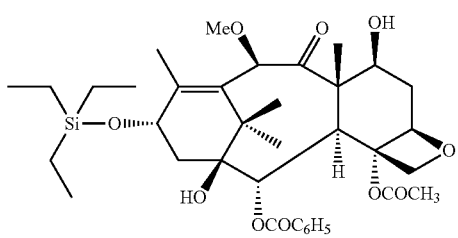

(XII)

The compound of Formula (XII) is chemically 4α-acetoxy-2α-benzoyloxy-5β,20-epoxy-1β,7β-dihydroxy-9-oxo-10β-methoxy-13β-triethylsilyloxy)-11-taxene.

The fourth aspect of the present invention relates to a novel intermediate of compound of Formula (XIII)

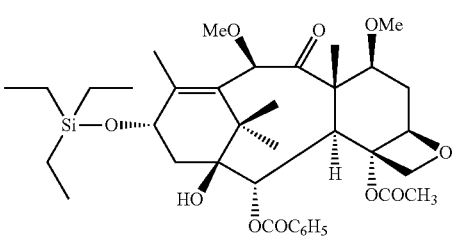

(XIII)

The compound of Formula (XIII) is chemically 4α-acetoxy-2α-benzoyloxy-5β,20-epoxy-1β-hydroxy-7β,10β-dimethoxy-9-oxo-13β-triethylsilyloxy)-11-taxene.

The fifth aspect of the present invention provides Isopropanol Solvate of Cabazitaxel (I).

BRIEF DESCRIPTION OF THE ACCOMPANYING DRAWINGS

Figure 2:
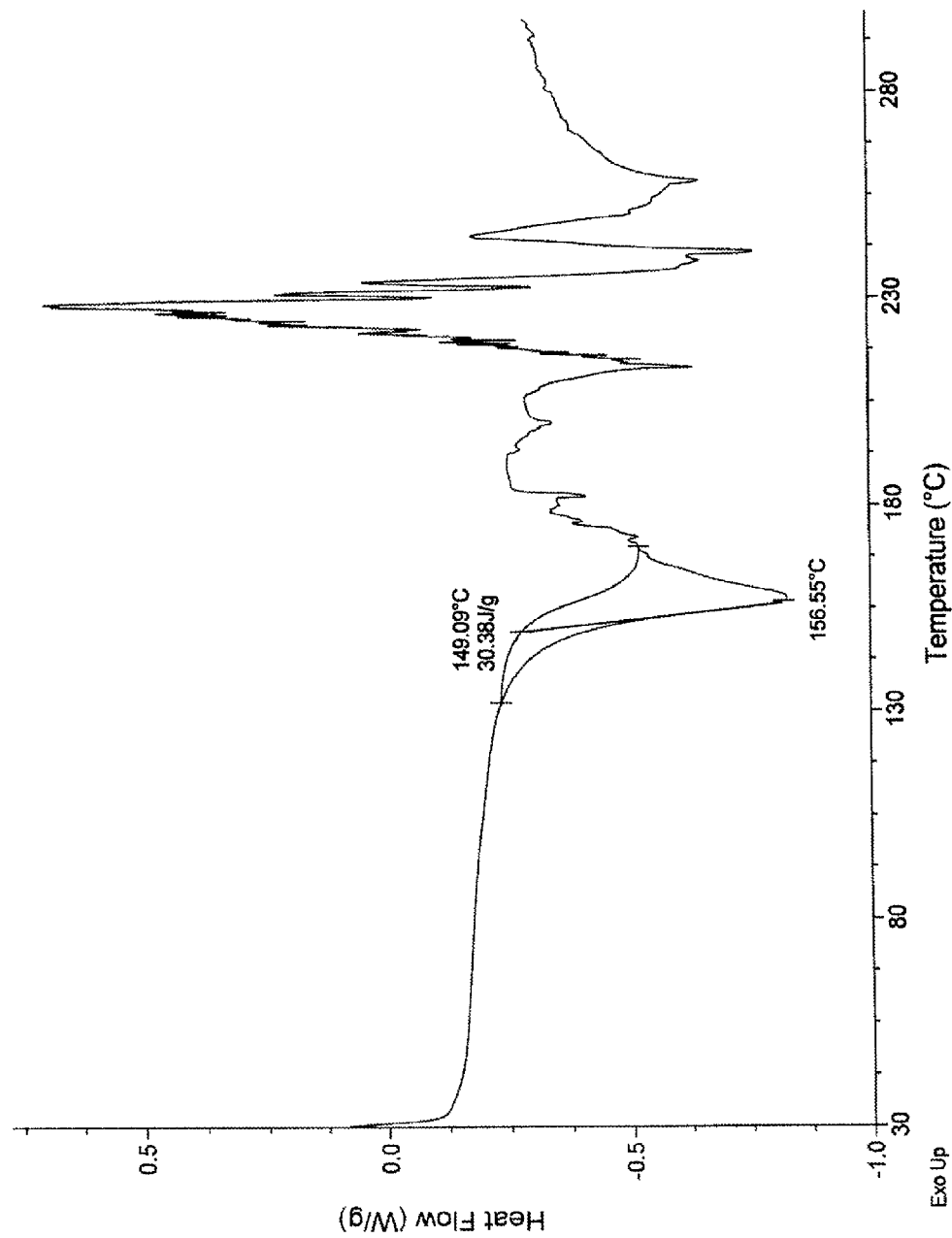
Figure 3:
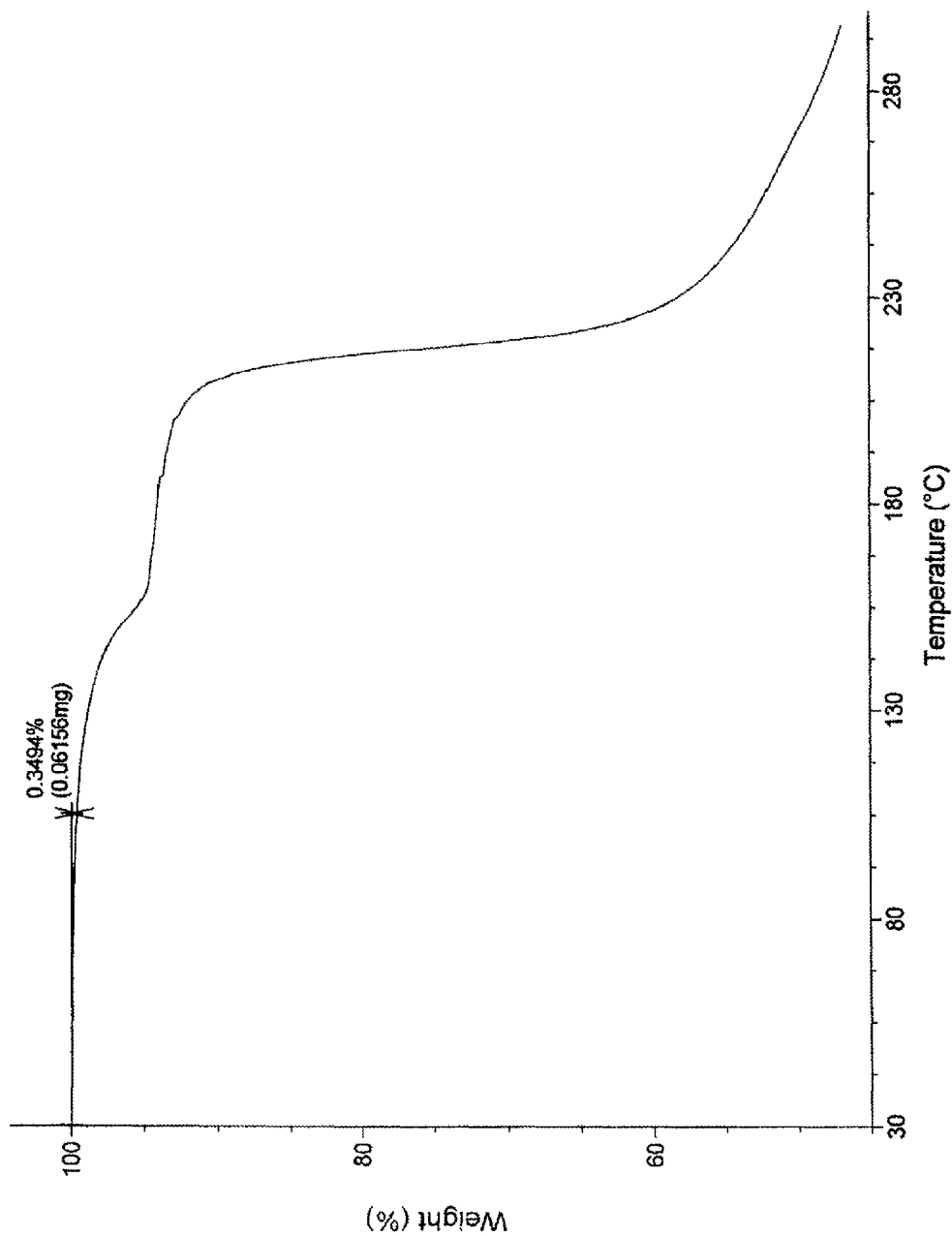

FIG. 1, which represents the X-ray (powder) diffraction pattern of the Isopropanol Solvate of Cabazitaxel of the present invention FIG. 2, which represents the Differential Scanning calorimetry (DSC) of the Isopropanol Solvate of Cabazitaxel of the present invention FIG. 3, which represents the TGA of the Isopropanol Solvate of Cabazitaxel of the present invention

DETAILED DESCRIPTION OF THE INVENTION 10-deacetyl baccatin III of Formula (III) may be obtained by any of the methods known in the art such as those described in U.S. Pat. No. 5,393,895, U.S. Pat. No. 5,736,366, U.S. Pat. No. 6,124,482 and U.S. Pat. No. 5,453,521.

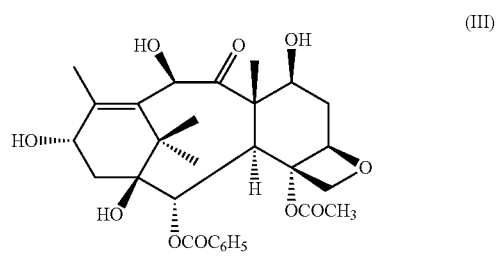

(III)

The silylation of Formula III in steps a) of the first and second process may be carried out by using a silylating agent.

The silylating agent may be selected from the group comprising of trimethyl silyl Halide, triethyl silyl Halide, tert-butyldimethylsilyl Halide, tri-iso-propylsilyloxymethyl Halide and triisopropyl silyl Halide.

The silylation of Formula III in the first and second process may be carried out in the presence of a base, which may be selected from the group comprising of organic or inorganic base.

The organic base may be selected from the group comprising of $C_1$-$C_4$ alkyl ammonia; mono, di or tri $C_1$-$C_4$ alkyl amine such as triethyl amine, diisopropropyl ethyl amine; mono, di or tri hydroxy $C_1$-$C_4$ alkyl amine; morpholine; thiomorpholine; piperidine; N,N-dimethylaniline, N.N-dimethylamino pyridine (DMAP), hydrazine, imidazole and pyrrolidine. The most preferred base is imidazole.

The inorganic base may be selected from the group comprising of metal carbonate such as lithium carbonate, sodium carbonate, potassium carbonate, barium carbonate, calcium carbonate and magnesium carbonate; metal bicarbonate such as sodium bicarbonate, potassium bicarbonate, barium bicarbonate, calcium bicarbonate and magnesium bicarbonate and metal hydroxide such as sodium hydroxide, potassium hydroxide, barium hydroxide, calcium hydroxide and magnesium hydroxide.

The silylation of Formula III in the first and second process may be carried out in the presence of a suitable solvent. Suitable solvent may be selected from the group comprising of: alcohols, such as methanol, ethanol and isopropanol; nitriles, such as acetonitrile; chlorinated hydrocarbons, such as methylene chloride, ethylene dichloride; dipolar aprotic solvents, such as dimethylsulfoxide and dimethylformamide; esters, such as ethyl acetate and isopropyl acetate; cyclic ethers, such as dioxane and tetrahydrofuran; and mixtures thereof. Most preferred solvent is methylene chloride.

The silylation of Formula III in the first and second process may be carried out a temperature range of from −15 to 60° C. and more preferably from 20 to 30° C. to give the silylated product.

The obtained silylated product can further be purified by using the suitable organic solvent such as methyl tert-butyl ether.

The silylation of Formula III in the first process may be carried out for about 1-10 hours and more preferably for 4-5 hours, thereby resulting in a product carrying only one silyl-group.

The silylation of Formula III in the second aspect may be carried out for about 15-30 hours and more preferably for 18-20 hours, thereby resulting in a product carrying two silyl-groups at two different positions.

Methylation of the hydroxyl function in steps b) and d) of first and second process may be carried out in the presence of methyl iodide, methyl sulfate, Diazomethane, dimethyl carbonate, methyl nitrate and the like. The most preferred methyl source is Methyl iodide.

Methylation of the hydroxyl function in steps b) and d) of first and second process may be carried out in the presence of an alkali metal hydride, such as sodium hydride, an alkali metal amide, such as lithium amide, or an alkali metal alkylide, such as butyl lithium.

Methylation of the hydroxyl group in steps b) and d) of first and second process may also be carried out in the presence of suitable solvent. A suitable solvent may be selected from the group comprising of water; alcohols, such as methanol, ethanol and isopropanol; nitriles, such as acetonitrile; chlorinated hydrocarbons, such as methylene chloride, ethylene dichloride; ethers, such as diethyl ether, isopropyl ether, methyl isobutyl ether; dipolar aprotic solvents, such as dimethylsulfoxide, dimethylformamide and dimethyl acetamide; esters, such as ethyl acetate and isopropyl acetate; cyclic ethers, such as dioxane and tetrahydrofuran; and mixtures thereof. Most preferred solvent is a mixture of methyl isobutyl ether and tetrahydrofuran.

Methylation of the hydroxyl group in steps b) and d) of first and second process may be carried out at a temperature range of from −5 to 50° C. and more preferably from −5 to 15° C.

The deprotection of the silyl group in step c) of first and second process may be carried out in the presence of an acid such as hydrofluoric acid or trifluoroacetic acid or fluorides such as tetrabutyl ammonium fluoride (TBAF).

The deprotection of the silyl group in step c) of first and second process may be carried out in the presence of a solvent such as tetrahydrofuran, acetonitrile, dichloromethane, methanol, ethanol and dimethylformamide.

The deprotection of the silyl group in step c) of first and second process may be carried out at a temperature range of from −5-50° C. and more preferably from −5 to 10° C.

The deprotection in step c) of the second process is performed such that one of the two protecting units, the one attached to the C7-OH is removed, and the other still remains and continuously protects the C13-OH. This is achieved by stirring the reaction mixture for about 2-8 hours. Most preferably for about 4-5 hours.

The esterification of compound of Formula (II) at C-13 Position may be carried out by using a method such as those described in the art for example in U.S. Pat. No. 5,637,723 and U.S. Pat. No. 5,847,170.

The esterification of compound of Formula (II) at C-13 Position by means of an acid of general formula (VII) may be carried out in the presence of a condensing/coupling agent reagent. A condensing reagent may be selected from the group comprising of carbodiimide such as dicyclocarbodiimide, Diisopropylcarbodiimide or ethyl-(N—N'-dimethyl amino propyl carbodiimide and reactive carbonates such as di-2-pyridyl carbonate and most preferred are carbodiimide.

The esterification of compound of Formula (II) at C-13 Position may be carried out in the presence of a catalyst. A catalyst may be selected from amino pyridines such as 4-dimethylaminopyridine or 4-pyrrolidinopyridine.

The esterification of compound of Formula (II) at C-13 Position may be carried out in the presence of a suitable solvent. Suitable solvent may be selected from the group comprising of water; alcohols, such as methanol, ethanol and isopropanol; nitriles, such as acetonitrile; chlorinated hydrocarbons, such as methylene chloride, ethylene dichloride; ethers, such as diethyl ether, isopropyl ether, methyl isobutyl ether; dipolar aprotic solvents, such as dimethylsulfoxide and dimethylformamide; esters, such as ethyl acetate and isopropyl acetate; cyclic ethers, such as dioxane and tetrahydrofuran; and mixtures thereof. The most preferred solvent is ethyl acetate.

The esterification of compound of Formula (II) at C-13 Position by means of an acid or salt of formula (VII) may be carried out at a temperature range of from 10-50° C. to obtain the compound of Formula (VIII).

Deprotection of the side chain of Formula (VIII) may be carried out at in the presence of an inorganic acid such as hydrochloric acid, sulphuric acid or nitric acid or organic acid such as acetic acid, methane sulphonic acid, trifluoromethane sulphonic acid or p-toluene sulphonic acid.

Deprotection of the side chain of Formula (VIII) may be carried out in the presence of a suitable solvent. Suitable solvent may be selected from the group comprising of water; alcohols, such as methanol, ethanol and isopropanol; nitriles, such as acetonitrile; chlorinated hydrocarbons, such as methylene chloride, ethylene dichloride; ethers, such as diethyl ether, isopropyl ether, methyl isobutyl ether; dipolar aprotic solvents, such as dimethylsulfoxide and dimethylformamide; esters, such as ethyl acetate and isopropyl acetate; cyclic ethers, such as dioxane and tetrahydrofuran; and mixtures thereof. Most preferred solvent is mixture of water and ethyl acetate.

Deprotection of the side chain of Formula (VIII) may be carried out at a temperature range of from −10 to 60° C., and preferably from 0-5° C. to obtain the compound of Formula (IX).

The compound of Formula IX, wherein $R_1$ is tertiary butoxy carbonyl, and wherein aryl is phenyl, is Cabazitaxel of Formula (I).

The Cabazitaxel obtained by the present invention may be in the Form of Isopropanol Solvate of Cabazitaxel.

The XRPD data reported herein was obtained using Cu Kα radiation, having the wavelength 1.541 Å and were obtained using Bruker AXS D8 advance Powder X-ray Diffractometer.

Isopropanol Solvate of Cabazitaxel may be characterized by its XRPD having peaks at diffraction angles 2-theta of about 7.3678, 7.8537, 8.9596, 10.2918, 12.5727, 12.8651, 13.3343, 13.5721, 14.4207, 14.7600, 15.1798, 15.3152, 15.6282, 15.7413, 16.5402, 16.9857, 17.6849, 17.9590, 18.3018, 18.6973, 18.7727, 19.4610, 20.4624, 20.6809, 21.1058, 21.1565, 21.4007, 21.7609, 21.9196, 22.2176, 23.1030, 23.5156, 23.7025, 24.2617, 24.7859, 25.1584, 25.8322, 26.3237, 27.0935, 27.4874, 27.7876, 28.3142, 28.9803, 30.1735, 30.6174, 31.2054, 31.5714, 32.2104, 32.3404, 32.9802±0.2.

Isopropanol Solvate of Cabazitaxel may be further characterized by its DSC curve having endothermic peak at about 156.98° C.

Isopropanol Solvate of Cabazitaxel may be further characterized by its TGA curve corresponding to a weight loss of about 0.3494% w/w.

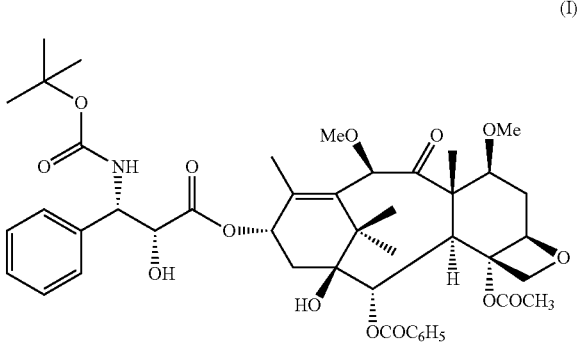

(I)

The compound of formula (XII) may be characterized by its NMR bands at about δ 0.65 (m, 9H), 0.96 (s, 3H), 0.99 (s, 3H), 0.99 (t, J=8.4 Hz, 6H), 1.48 (s, 3H), 1.64 (m, 1H), 1.94 (s, 3H), 2.17 (m, 2H), 2.20 (s, 3H), 2.27 (m, 1H), 3.27 (s, 3H), 3.70 (d, J=7.2 Hz, 1H), 4.03 (bs, 2H), 4.11 (m, 1H), 4.52 (s, 1H, OH), 4.86 (s, 1H), 4.91 (m, 2H), 5.02 (d, J=7.2 Hz, 1H, OH), 5.40 (d, J=7.2 Hz, 1H), 7.55 (t, J=7.2 Hz, 2H), 7.66 (t, J=7.2 Hz, 1H), 8.0 (d, J=7.2 Hz, 2H) and further characterized by Mass spectra at 673 (M+H)⁺.

The compound of formula (XIII) may be characterized by its NMR bands at about δ 0.65 (m, 6H), 0.95 (s, 3H), 0.99 (s, 3H), 0.99 (t, J=8.0 Hz, 9H), 1.48 (m, 1H), 1.52 (s, 3H), 1.97 (s, 3H), 2.10-2.22 (m, 2H), 2.21 (s, 3H), 2.66 (m, 1H), 3.21 (s, 3H), 3.30 (s, 3H), 3.70 (d, J=6.8 Hz, 1H), 3.80 (dd, J=10.4 Hz & 6.4 Hz, 1H), 4.03 & 4.06 (2×d, J=7.6 Hz, 2H), 4.56 (s, 1H, OH), 4.72 (s, 1H), 4.87 (m, 1H), 4.97 (d, J=5.6 Hz, 1H), 5.38 (d, J=7.2 Hz, 1H), 7.55 (t, J=7.2 Hz, 2H), 7.66 (t, J=7.2 Hz, 1H), 7.99 (d, J=7.2 Hz, 2H) and further characterized by Mass spectra at: 687 (M+H)¹.

Detailed experimental parameters suitable for this novel process of making Cabazitaxel are provided by the following examples, which are intended to be illustrative and not limiting of all possible embodiments of the invention.

EXAMPLES

Example 1

Synthesis of 4α-acetoxy-2α-benzoyloxy-5β,20-epoxy-1β,10β,13α-trihydroxy-9-oxo-7β-triethylsilyloxy-11-taxene

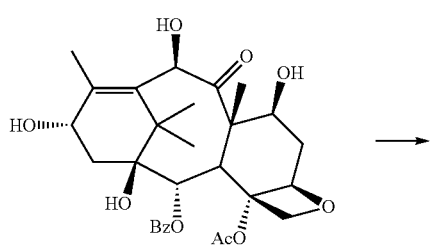 → 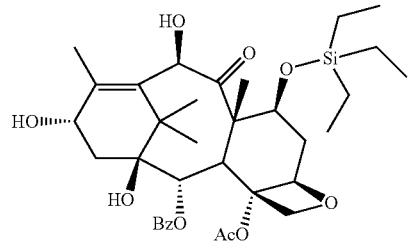

100 g of 10-DAB is charged at 20-25° C. and cooled to 0-5° C. 37.52 g of Imidazole is charged at 0-5° C. and stirred. After stirring for 10-15 min, the solution of 55.30 g triethyl silyl chloride in 100 ml methylene chloride is added at 0-5° C. and stirred for 30-40 min. The reaction mixture is brought to a room temperature and stirred for 4-5 hrs. Reaction is diluted with 500 ml of DM water and stirred for 10-20 min. The organic phase is separated and washed twice with 250 ml of DM water. The organic phase is again washed with 200 ml 10% NaCl solution and organic phase is again separated and concentrated at below 40° C. till organic layer reduced half. n-hexane is charged to the residue and stirred for 30-40 min at 20-25° C. The slurry is filtered and washed twice with 200 ml n-hexane. Product is dried at 50-55° C. for 6-8 h to get 113 g 4α-acetoxy-2α-benzoyloxy-5β,20-epoxy-1β,10β,13α-trihydroxy-9-oxo-7β-triethylsilyloxy)-11-taxene.

Yield: 93.4%

Example 2

Synthesis of 4α-acetoxy-2α-benzoyloxy-5β,20-epoxy-1β,10β,13α-trihydroxy-9-oxo-7β-triethylsilyloxy-11-taxene 7.7 liter dichloromethane and 936.9 g of imidazole is charged. Reaction mixture is heated to 20-25° C. and stirred for 15-30 min. 50 g 10-DAB and 2.5 liter of 10-DAB were charged to the reaction mixture and stirred for 1 h at 20-30° C. In a separate container 2.5 L of Dichloromethane and 207.4 g of triethylsilyl chloride were added. This mixture is slowly added to the reaction mixture within 1-2 hrs at 20-30° C. Reaction mixture is stirred for further 4-5 hours. 2.5 L of purified water is added and stirred for 5-10 min. The organic layer is separated and treated with aqueous HCl (250 ml HCl is dissolved in 2.5 l of water). After stirring for 5-10 min the organic layer is separated. 2.5 l of water is added to the organic layer and again stirred for 5-10 min. The organic layer is separated and filtered through micron filter. The layer is concentrated under reduced pressure below 40° C. to get the solid product. To this solid 2.0 l of methyl tertiary butyl ether is charged and stirred for 5-10 min. the solution is cooled to 0 to 5° C. and stirred at the same temperature for 1 h. the solid is filtered and washed with methyl tert-butyl ether (250×2). The wet cake is suck dried for 1 h and obtained solid material is dried at 40-50° C. under vacuum for 4-6 h to get 556 g of 4α-acetoxy-2α-benzoyloxy-5β,20-epoxy-1β,10β,13α-trihydroxy-9-oxo-7(3-triethylsilyloxy)-11-taxene.

Yield: 91.7%

Chromatographic purity: 91.7%

Example 3

Synthesis of 4α-acetoxy-2α-benzoyloxy-5β,20-epoxy-1β,13α-dihydroxy-10β-methoxy-9-oxo-7β-triethylsilyloxy-11-taxene

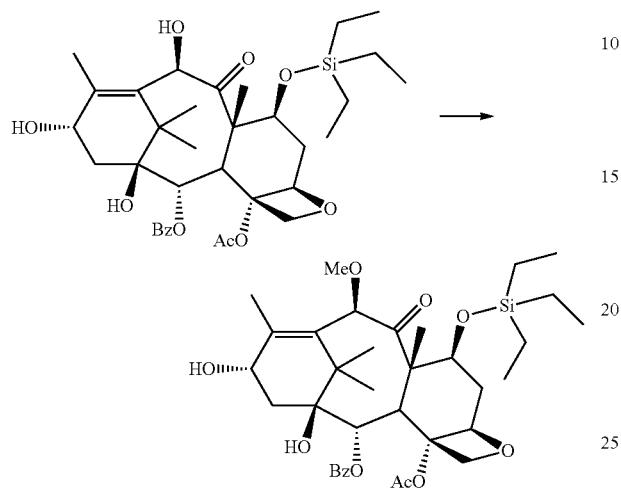

25 g of 4α-acetoxy-2α-benzoyloxy-5β,20-epoxy-1β,10β,13α-trihydroxy-9-oxo-7β-triethyl silyloxy-11-taxene, 125 ml of methyl tert-butyl ether and 50 ml of THF were added and stirred at 20-25° C. for 10 min. Reaction mixture is brought to a temperature of −5° C. to 0° C. and 7.59 g of sodium hydride is added to the reaction mixture and stirred at −5 to 0° C. for 18-20 h. The reaction mixture is diluted by adding 150 ml of dichloromethane and stirred for 10-20 min. A solution of 13.68 ml of acetic acid in 10 ml dichloromethane is added drop wise to the reaction mixture at 0-5° C. and stirred for 20-30 min followed by the addition of DM water and stirred for 10-15 min at 10-20° C. The organic phase is separated and washed with 100 ml DM water twice and with 50 ml 10% NaCl solution and concentrated below 40° C. to get 24.2 g solid.

$^1$H NMR (400 MHz; CDCl$_3$, ppm) δ: 8.10 (d, J=8.0 Hz, 2H), 7.59 (t, J=7.2 Hz, 1H), 7.45 (t, J=7.6 Hz, 2H), 5.60 (d, J=7.2 Hz, 1H), 4.90-4.97 (m, 3H), 4.43 (dd, J=7.2 & 10.8 Hz, 1H), 4.30 (d, J=8.4 Hz, 1H), 4.15 (d, J=8.4 Hz, 1H), 3.88 (d, J=6.8 Hz, 1H), 3.41 (s, 3H), 2.42-2.52 (m, 1H), 2.27-2.28 (m, 4H), 2.11 (s, 3H), 2.03 (d, J=5.6 Hz, 1H), 1.86-1.92 (m, 1H), 1.68 (s, 3H), 1.58 (brs, 1H, OH), 1.17 (s, 3H), 1.07 (s, 3H), 0.96 (t, J=8.0 Hz, 9H), 0.57 (m, 6H)

MS (ES$^+$) m/z: 673 (M+H)$^+$

Yield: 95%

Example 4

Synthesis of 4α-acetoxy-2α-benzoyloxy-5β,20-epoxy-1β,13α-dihydroxy-10β-methoxy-9-oxo-7β-triethylsilyloxy-11-taxene 556 g of 4α-acetoxy-2α-benzoyloxy-5β,20-epoxy-1β,10β,13α-trihydroxy-9-oxo-7β-triethylsilyloxy-11-taxene, 1.39 l of dimethyl acetamide and stirred at −5 to −15° C. 359.4 g of methyl iodide and 7.59 g of sodium hydride is added to the reaction mixture at the same temperature and stirred for one hour. 10.15 g of sodium hydride is again charged to the reaction mixture and reaction mixture is stirred for 4-5 h at −5 to −15° C. Acetic acid 67.6 ml is slowly added to the reaction to bring the pH≤7. Purified water 2.78 l is added slowly to the reaction mixture. The reaction mixture is stirred for 1-2 hour at 20-30° C. The precipitated mass is filtered and wet cake is washed with water (2.78×3). The wet cake is dried for 2 hour. The solid material is dried at 50-60° C. under vacuum for 4-6 hrs to get 560 g of 4α-acetoxy-2α-benzoyloxy-5β,20-epoxy-1β,13α-dihydroxy-10β-methoxy-9-oxo-7β-triethylsilyloxy-11-taxene.

Example 5

Synthesis of 4α-acetoxy-2α-benzoyloxy-5β,20-epoxy-10β-methoxy-9-oxo-1β,13α,7β-trihydroxy-11-taxene

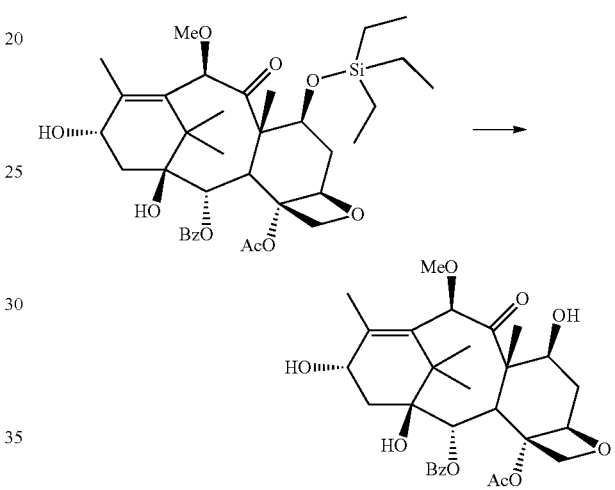

125 ml of THF is added to the 25 g of 4α-acetoxy-2α-benzoyloxy-5β,20-epoxy-1β,13α-dihydroxy-10β-methoxy-9-oxo-7β-triethylsilyloxy-11-taxene. After stirring at 20-25° C. for 5-10 min, reaction mixture is cooled to 0-5° C. 55.8 ml of tetrabutyl ammonium fluoride (TBAF) is added to the reaction mixture and after the stirring for 4-5 hrs, a solution of 3.35 ml acetic acid in 250 ml DM water is added at 20-25° C. and reaction mixture is stirred for 10-20 min. Reaction mixture is diluted with 250 ml of ethyl acetate and the aqueous phase is separated and extracted with 250 ml ethyl acetate. The organic layer were mixed, dried over sodium sulphate and filtered. The organic layer is concentrated at below 45° C. n-hexane is added to the slurry and stirred for 1-1.5 h at room temperature. The solid is filtered and washed twice with n-hexane. The product is dried under vacuum at 50-55° C. for 20-24 h to obtain 17 g of 4α-acetoxy-2α-benzoyloxy-5β,20-epoxy-10β-methoxy-9-oxo-1β,13α,7β-trihydroxy-11-taxene.

Yield: 81.9%

Example 6

Synthesis of 4α-acetoxy-2α-benzoyloxy-5β,20-epoxy-10β-methoxy-9-oxo-1β,13α,7β-trihydroxy-11-taxene 3.892 liter of THF is added to the 25 g of 4α-acetoxy-2α-benzoyloxy-5β,20-epoxy-1β,13α-dihydroxy-10β-methoxy-9-oxo-7β-triethylsilyloxy-11-taxene. After stirring at 20-25°

C. for 5-10 min, reaction mixture is cooled to 0-5° C. 1.69 ml of tetrabutyl ammonium fluoride (TBAF) is added to the reaction mixture and after the stirring for 4-5 hrs at 0-5° C., a solution of 106.2 ml acetic acid 19.46 L water is added. The contents were cooled at 0-5° C. and stirred for 1-2 h. The obtained solid is filtered and washed with purified water. The material is suck dried for 2-3 h at room temperature and then dried at 50-60° C. under vacuum for 4-6 hrs. The solid material is treated with 3.63 l of ethyl acetate. The contents were heated 40-50° C. and concentrated under vacuum at 50° C. to get the solid product. 730 ml of methyl tertiary butyl ether is charged to the solid and stirred at 20-30° C. The solid is filtered and washed with 370 ml of methyl tertiary butyl ether. The material is first dried at room temperature for 30 min and then dried under vacuum at 40-50° C. for 4-6 hrs.

Yield=72.9%,

Chromatographic purity: 97.95%.

Example 7

Synthesis of 4α-acetoxy-2α-benzoyloxy-5β,20-epoxy-1β,13α-dihydroxy-7β,10β-dimethoxy-9-oxo-11-taxene

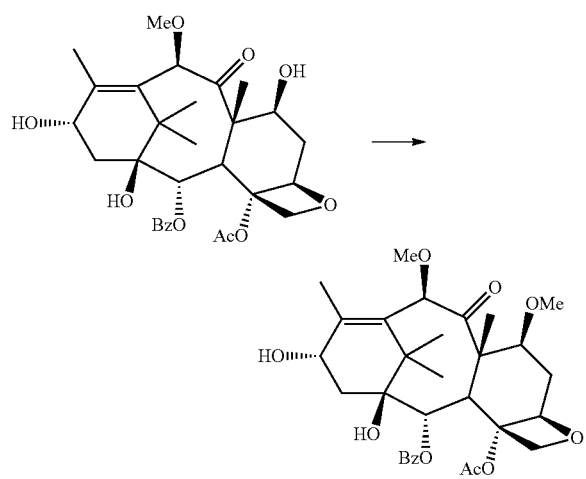

The solution of 10 g of 4α-acetoxy-2α-benzoyloxy-5β,20-epoxy-10β-methoxy-9-oxo-1β,13α,7β-trihydroxy-11-taxene in 60 ml dimethyl acetamide is stirred till the clear solution and cooled to −10 to −15° C. 1.49 g of sodium hydride is added to the reaction mixture followed by the drop wise addition of 7.31 g methyl iodide. Reaction mixture is stirred for 3.5 to 4 h at −10 to −15° C. Reaction mixture is poured in 60 ml 20% aq NH₄Cl solution at 20-22° C. and stirred for 15-10 min at −10 to −15° C. 350 ml of water is added to the reaction mixture. Obtained solid is filtered and washed with 20 ml and dried for 20 min. crude material is purified by using 50 ml ethyl acetate and 15 ml hexane to get 5.35 g of 4α-acetoxy-2α-benzoyloxy-5β,20-epoxy-1β,13α-dihydroxy-7β,10β-dimethoxy-9-oxo-11-taxene.

Yield: 52%

Example 8

Synthesis of 4α-acetoxy-2α-benzoyloxy-5β,20-epoxy-1β,13α-dihydroxy-7β,10β-dimethoxy-9-oxo-11-taxene The solution of 325 g of 4α-acetoxy-2α-benzoyloxy-5β,20-epoxy-10β-methoxy-9-oxo-1β,13α,7β-trihydroxy-11-taxene in 1.95 liter is cooled at −10 to −15° C. 734.5 g of methyl iodide and 23.3 g of sodium hydride were charged to the reaction mixture. Reaction mixture is stirred for one hour at −5 to −15° C. 17.17 g of sodium hydride is charged to the reaction mixture and reaction mixture is stirred for 4-5 h at the same temperature. To this solution 104.8 ml of acetic acid is added slowly and stirred for 30 min. to this reaction mixture 3.25 liter of purified water is added and reaction mixture is stirred for 4 h at 20-30° C. The reaction mass is filtered and wet cake is washed with purified water (1.625×2) and methanol (325×2). The wet cake is treated with 4.06 liter of methanol (325×2) and solid material is filtered and again washed with methanol. The obtained solid material is dried under vacuum at 40-50° C. for 4-6 hrs to get 4α-acetoxy-2α-benzoyloxy-5β,20-epoxy-1β,13α-dihydroxy-7β,10β-dimethoxy-9-oxo-11-taxene.

Yield=58.8%

Chromatographic Purity: 97.13%

Example 9

Synthesis of 4α-acetoxy-2α-benzoyloxy-5β,20-epoxy-1β,10β-dihydroxy-9-oxo-7β, 13β-di(triethylsilyloxy)-11-taxene

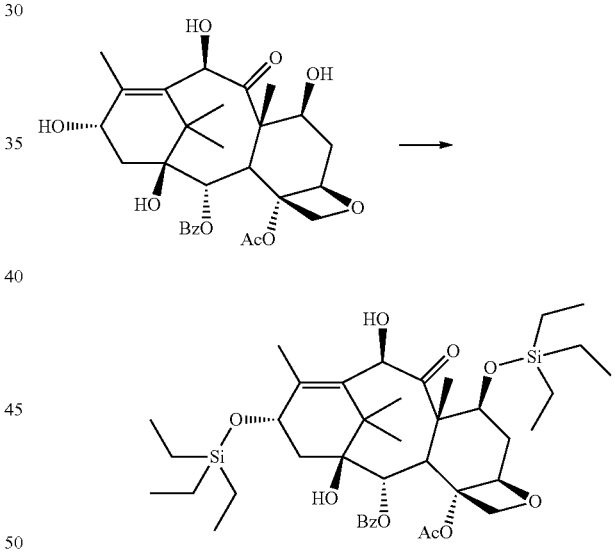

30 g of 10-DAB is charged at 20-25° C. and cooled to 0-5° C. under an argon atmosphere. 18.7 g of Imidazole and 6.7 g of DMAP is charged at 0-5° C. and stirred. A solution of 41.5 g triethylsilyl chloride in 50 ml DCM is added at 0-5° C. The reaction mixture is brought to a room temperature and stirred for 18-20 hours. Reaction is diluted with 150 ml of DM water. The organic phase is separated and washed twice with 100 ml of DM water. The organic phase is separated and then concentrated till dryness. The product is purified by column chromatography using 5-15% solution of ethyl acetate and n-hexane. Fractions containing only the desired product were concentrated to dryness at below 40° C. to get 25.5 g of 4α-acetoxy-2α-benzoyloxy-5β,20-epoxy-1β,10β-dihydroxy-9-oxo-7β, 13β-di(triethylsilyloxy)-11-taxene.

Yield: 59.8%

Example 10

Synthesis of 4α-acetoxy-2α-benzoyloxy-5β,20-epoxy-1β-hydroxy-9-oxo-10β-methoxy-7β, 13β-di(triethylsilyloxy)-11-taxene

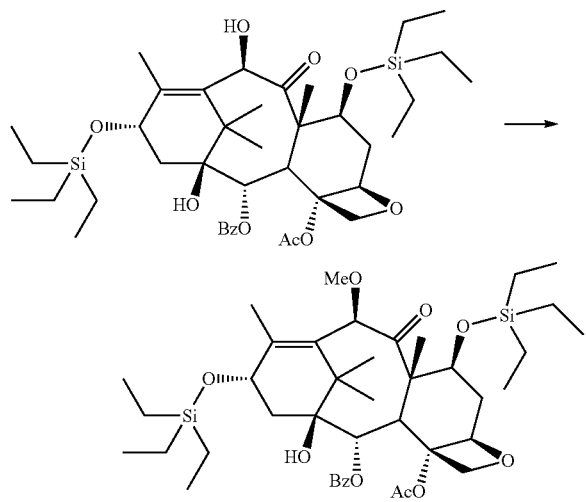

96 ml of methyl iodide is added to 24 g of 4α-acetoxy-2α-benzoyloxy-5β,20-epoxy-1β,10β-dihydroxy-9-oxo-7β,13β-di(triethylsilyloxy)-11-taxene at 20-25° C. and stirred at 0-5° C. 24 ml THF is added and stirred at 0-5° C. 2.98 g of sodium hydride is added to the reaction mixture and stirred at −5 to 0° C. The reaction mixture is diluted by adding a solution of 7.45 g acetic acid in 100 ml dichloromethane and stirred for 10-20 min at 0-5° C., followed by the addition of 50 ml DM water. The organic phase is separated and washed with 40 ml DM water. The organic layer is separated and concentrated till solid appears. The solid material is crystallized by using 50 ml ethyl acetate and 300 ml n-hexane. The slurry is filtered and dried under vacuum at 30-40° C. to get 19 g of 4α-acetoxy-2α-benzoyloxy-5β,20-epoxy-1β-hydroxy-9-oxo-10β-methoxy-7β,13β-di(triethylsilyloxy)-11-taxene.

Yield: 77.7%

Example 11

Synthesis of 4α-acetoxy-2α-benzoyloxy-5β,20-epoxy-1β,7β-dihydroxy-9-oxo-10β-methoxy-13β-triethylsilyloxy)-11-taxene

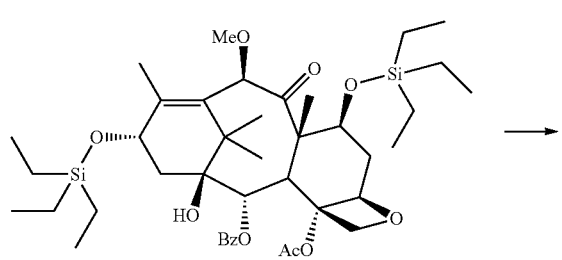

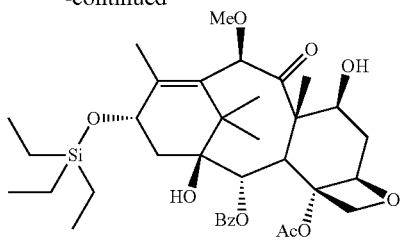

36 ml of THF is added to the 12 g of 4α-acetoxy-2α-benzoyloxy-5β,20-epoxy-1β-hydroxy-9-oxo-10β-methoxy-7β,13β-di(triethylsilyloxy)-11-taxene. After the stirring at 0-5° C. under nitrogen, 18.3 ml of tetrabutyl ammonium fluoride (TBAF) is added to the reaction mixture and stirred for 4-5 hrs at 0-5° C. Reaction mixture is diluted by adding 10 ml dichloromethane and 30 ml DM water. The organic layer is separated and washed with 20 ml DM water. Organic layer is concentrated to obtain solid residue. The solid residue is purified by column chromatography using 20-40% solution of ethyl acetate and hexane. Fractions containing only the desired product were concentrated to dryness at below 40° C. to get 8.3 g of 4α-acetoxy-2α-benzoyloxy-5β,20-epoxy-1β,7β-dihydroxy-9-oxo-10β-methoxy-13β-triethylsilyloxy)-11-taxene.

Yield: 86.5%

Spectral Data:

$^1$H NMR (400 MHz; DMSO-$d_6$, ppm) δ: 0.65 (m, 9H), 0.96 (s, 3H), 0.99 (s, 3H), 0.99 (t, J=8.4 Hz, 6H), 1.48 (s, 3H), 1.64 (m, 1H), 1.94 (s, 3H), 2.17 (m, 2H), 2.20 (s, 3H), 2.27 (m, 1H), 3.27 (s, 3H), 3.70 (d, J=7.2 Hz, 1H), 4.03 (bs, 2H), 4.11 (m, 1H), 4.52 (s, 1H, OH), 4.86 (s, 1H), 4.91 (m, 2H), 5.02 (d, J=7.2 Hz, 1H, OH), 5.40 (d, J=7.2 Hz, 1H), 7.55 (t, J=7.2 Hz, 2H), 7.66 (t, J=7.2 Hz, 1H), 8.0 (d, J=7.2 Hz, 2H).

MS (ES$^+$) m/z: 673 (M+H)$^+$

Example 12

Synthesis of 4α-acetoxy-2α-benzoyloxy-5β,20-epoxy-1β-hydroxy-7β,10β-dimethoxy-9-oxo-13β-triethylsilyloxy)-11-taxene

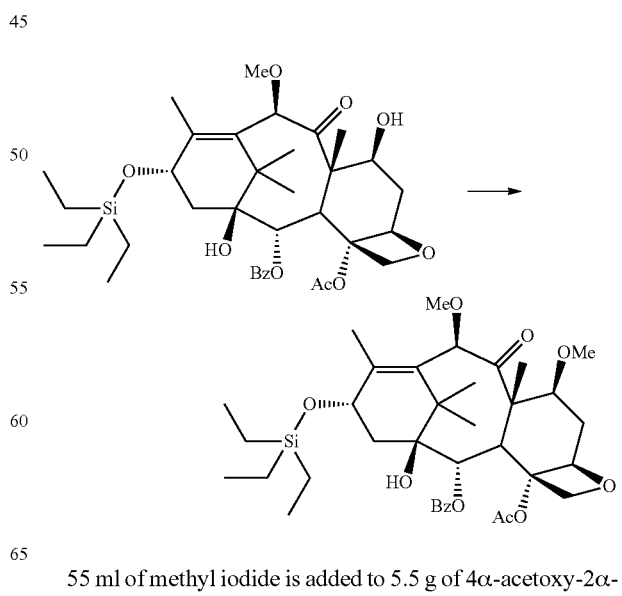

55 ml of methyl iodide is added to 5.5 g of 4α-acetoxy-2α-benzoyloxy-5β,20-epoxy-1β,7β-dihydroxy-9-oxo-10β- methoxy-13β-triethylsilyloxy)-11-taxene at 20-25° C. 5.5 ml THF is added and stirred at 0-5° C. 0.65 g of sodium hydride is added to the reaction mixture and stirred at −5 to 0° C. The reaction mixture is diluted by adding a solution of 0.93 g acetic acid in 6 ml dichloromethane and stirred for 10-20 min at 0-5° C., followed by the addition of 38.5 ml DM water. The organic phase is separated and washed with 30 ml DM water. The organic layer is separated and concentrated till solid appears. The solid material purified by column chromatography by using 5-25% solution of ethyl acetate and hexane to get 4.5 g 4α-acetoxy-2α-benzoyloxy-5β,20-epoxy-1β-hydroxy-7β,10β-dimethoxy-9-oxo-13β-triethylsilyloxy)-11-taxene.

Yield: 76.6%

Spectral Data:
$^1$H NMR (400 MHz; DMSO-d$_6$, ppm) δ: 0.65 (m, 6H), 0.95 (s, 3H), 0.99 (s, 3H), 0.99 (t, J=8.0 Hz, 9H), 1.48 (m, 1H), 1.52 (s, 3H), 1.97 (s, 3H), 2.10-2.22 (m, 2H), 2.21 (s, 3H), 2.66 (m, 1H), 3.21 (s, 3H), 3.30 (s, 3H), 3.70 (d, J=6.8 Hz, 1H), 3.80 (dd, J=10.4 Hz & 6.4 Hz, 1H), 4.03 & 4.06 (2×d, J=7.6 Hz, 2H), 4.56 (s, 1H, OH), 4.72 (s, 1H), 4.87 (m, 1H), 4.97 (d, J=5.6 Hz, 1H), 5.38 (d, J=7.2 Hz, 1H), 7.55 (t, J=7.2 Hz, 2H), 7.66 (t, J=7.2 Hz, 1H), 7.99 (d, J=7.2 Hz, 2H).

MS (ES$^+$) m/z: 687 (M+H)$^+$

Example 13

Synthesis of 4α-acetoxy-2α-benzoyloxy-5β,20-epoxy-1β,13α-dihydroxy-7β,10β-dimethoxy-9-oxo-11-taxen

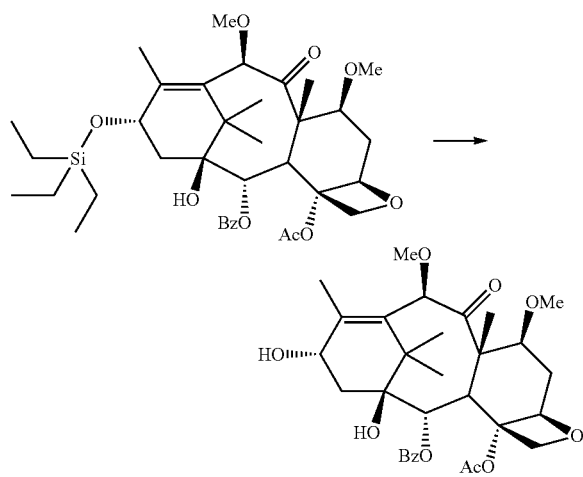

19.8 ml of THF is added to the 4.3 g of 4α-acetoxy-2α-benzoyloxy-5β,20-epoxy-1β-hydroxy-7β,10β-dimethoxy-9-oxo-13β-triethylsilyloxy)-11-taxene. After the stirring at 0-5° C. under nitrogen, 9.4 ml of tetrabutyl ammonium fluoride (TBAF) is added to the reaction mixture and stirred for 4-5 hrs at 0-5° C. Reaction mixture is concentrated under vacuum at below 25° C. to nearly the half volume. Reaction mixture is diluted by adding a solution of 0.1 ml acetic acid in 50 ml water. The slurry is filtered and solid material is washed with 30 ml DM water. The filtrate is extracted by using 50 ml ethyl acetate. Organic layer is concentrated to dryness and refluxed with 100 ml ethyl acetate. The slurry is filtered and solid material is dried under vacuum at 40-45° C. to get 1.05 g 4α-acetoxy-2α-benzoyloxy-5β,20-epoxy-1β,13α-dihydroxy-7β,10β-dimethoxy-9-oxo-11-taxen.

Yield: 29.3%

Example 14

Synthesis of 4α-acetoxy-2α-benzoyloxy-5β,20-epoxy-1β,13α-dihydroxy-7β,10β-dimethoxy-9-oxo-11-taxen-13α-yl-(2R,4S,5S)-3-tert-butoxycarbonyl-2-(4-methoxyphenyl)-4-phenyl-1,3-oxazolidine-5-carboxylate

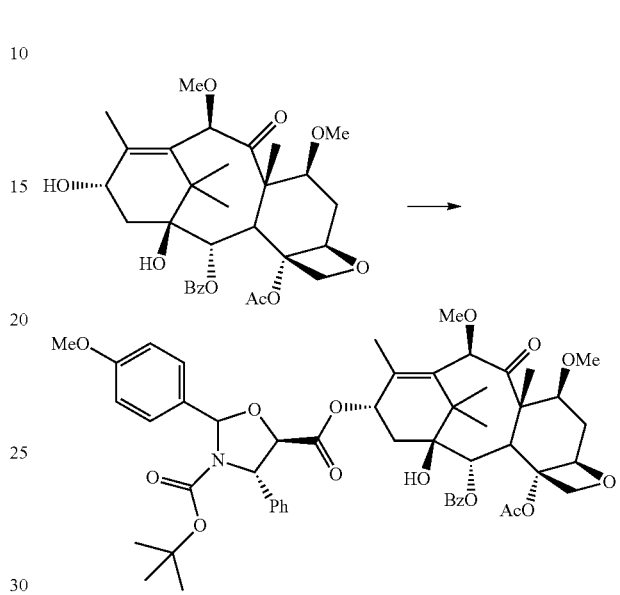

0.78 g of dicyclohexylcarbodiimide and 0.085 g of 4-(N,N-dimethylamino)pyridine were added successively at 20-25° C. to a suspension containing 1.35 g of 4α-acetoxy-2a-benzoyloxy-5β,20-epoxy-1β,13α-dihydroxy-7β,10β-dimethoxy-9-oxo-11-taxene, 1.41 of (2R,4S,5S)-3-tert-butoxycarbonyl-2-(4-methoxyphenyl)-4-phenyl-1,3-oxazolidine-5-carboxylic acid in 12 ml of ethyl acetate. Reaction mixture is stirred for 48 h at 20-25° C. Reaction mixture is diluted with 50 ml DM water and ethyl acetate. Organic phase is separated and washed with 20 ml 5% NaHCO$_3$ solution followed by the filtration. Organic phase is concentrated under reduced pressure at 40° C. The residue obtained is purified by chromatography on 100 g silica gel using 10% solution of ethyl acetate and n-hexane. Fractions containing only the desired product were concentrated to dryness at below 40° C. to get 1.2 g 4α-acetoxy-2α-benzoyloxy-5β,20-epoxy-1β,13α-dihydroxy-7β,10β-dimethoxy-9-oxo-11-taxen-13α-yl-(2R,4S,5S)-3-tert-butoxycarbonyl-2-(4-methoxyphenyl)-4-phenyl-1,3-oxazolidine-5-carboxylate.

Yield: 75%

Example 15

Synthesis of 4α-acetoxy-2α-benzoyloxy-5β,20-epoxy-1β,13α-dihydroxy-7β,10β-dimethoxy-9-oxo-11-taxen-13α-yl-(2R,4S,5S)-3-tert-butoxycarbonyl-2-(4-methoxyphenyl)-4-phenyl-1,3-oxazolidine-5-carboxylate 190 g of 4α-acetoxy-2a-benzoyloxy-5β,20-epoxy-1β,13α-dihydroxy-7β,10β-dimethoxy-9-oxo-11-taxene is dissolved in 3.8 l of tetrahydrofuran and stirred for 30 min at 20-30° C. Charged 20.24 g of 4-(N,N-dimethylamino)pyridine (DMAP) and 198.8 g of (2R,4S,5S)-3-tert-butoxycarbonyl-2-(4-methoxyphenyl)-4-phenyl-1,3-oxazolidine-5-carboxylic acid to the reaction mix and stirred at 20-30° C. for 30 min. To this reaction mixture 83.7 g of diisopropylcarbodiimide is added and reaction mixture is stirred for 4-5 hour. The solid is filtered and washed with tetrahydrofuran (425× 2). The filtrate is charged in 5.13 L of water and reaction mass is stirred for 3-4 hours at 20-30° C. The solid is filtered and washed with water (425×2). The solid is again washed with 570 ml methanol and suck dried for 2 h. The solid is again treated with 1.33 liter methanol by heating to reflux for 2 hours. The solution is cooled to room temperature and solid is filtered. The solid is washed with 570 ml of methanol and suck dried for 1 hour. The material is dried under vacuum for 4-6 h at 40-50° C. to get 260 g of 4α-acetoxy-2α-benzoyloxy-5β,20-epoxy-1β,13α-dihydroxy-7β,10β-dimethoxy-9-oxo-11-taxen-13α-yl-(2R,4S,5S)-3-tert-butoxycarbonyl-2-(4-methoxyphenyl)-4-phenyl-1,3-oxazolidine-5-carboxylate.

Yield: 82.5%

Chromatographic Purity: 98.84%

Example 16

Synthesis of Cabazitaxel

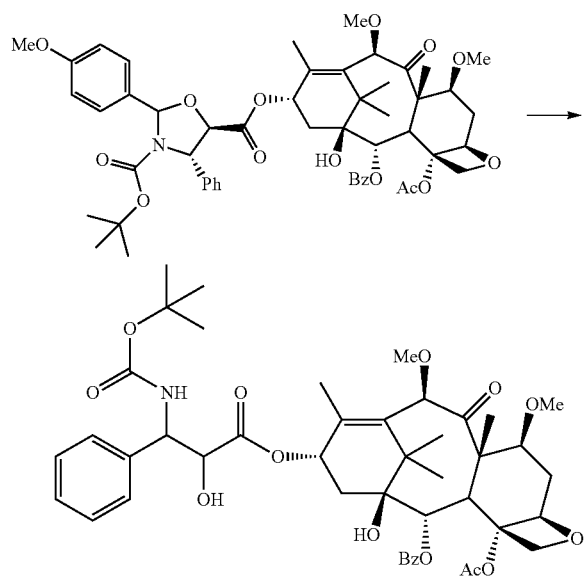

A solution of 1.6 g of 4α-acetoxy-2α-benzoyloxy-5β,20-epoxy-1β,13α-dihydroxy-7β,10β-dimethoxy-9-oxo-11-taxen-13α-yl-(2R,4S,5S)-3-tert-butoxycarbonyl-2-(4-methoxyphenyl)-4-phenyl-1,3-oxazolidine-5-carboxylate in 15 ml ethyl acetate and 12 ml solution of 0.25 N ethylacetate and HCl is stirred at 0° C. for overnight. The reaction mixture is then diluted with 20 ml ethyl acetate and washed with 15 ml NaHCO$_3$ solution. The organic phase is concentrated till the dryness under vacuum at below 40° C. The product is purified by column chromatography on 100 g silica gel using 10% solution of 500 ml ethyl acetate and n-hexane. Fractions containing only the desired product were concentrated to dryness at below 40° C. to get 1.0 g of 4α-acetoxy-2α-benzoyloxy-5β,20-epoxy-1β,13α-dihydroxy-7β,10β-dimethoxy-9-oxo-11-taxen-13α-yl-(2R,4S,5S)-3-tert-butoxycarbonylamino-2-hydroxy-3-phenylpropionate.

Yield: 71%

Spectral Data:

$^1$H NMR (400 MHz; CDCl$_3$, ppm) δ: 1.20 (s, 3H, CH$_3$), 1.21 (s, 3H, CH$_3$), 1.35 (s, 9H, t-Bu), 1.69 (s, 1H, OH at position 1), 1.68 (s, 3H, CH$_3$), 1.76-1.79 (m, 1H, CH$_{6a}$H$_{6b}$), 1.87 (s, 3H, CH$_3$), 2.24-2.29 (m, 2H, CH$_2$ 16), 2.35 (s, 3H, COCH$_3$), 2.67-2.70 (m, 1H, CH$_{6a}$H$_{6b}$), 3.30 (s, 3H, OCH$_3$), 3.45 (s, 3H, OCH$_3$), 3.45 (brs, 1H, OH at position 2'), 3.80 (d, J=6.8 Hz, 1H, H3), 3.85 (dd, J=10.0 & 6.0 Hz, 1H, H7), 4.17 & 4.29 (2d, J=8.4 Hz, 1H each, CH$_{20a}$H$_{20b}$ & CH$_{20a}$H$_{20b}$), 4.62 (brs, 1H, H-2'), 4.79 (s, 1H, H-10), 4.96 (d, J=8.8 Hz, 1H, H-5), 5.26 (d, J=7.6 Hz, 1H, H-3'), 5.43 (d, J=9.2 Hz, 1H, CONH), 5.62 (d, 6.8 Hz, 1H, H-2), 6.20 (t, 1H, H-13), 7.32-7.34 (m, 1H, aromatic proton), 7.38-7.42 (m, 4H, aromatic protons), 7.48 (t, 2H, OCOC6H5, H at meta position), 7.60 (t, 1H, OCOC$_6$H$_5$, H at para position) and 8.09 (d, J=7.2 Hz, 2H, OCOC$_6$H$_5$, H at ortho position)

MS (ES$^+$) m/z: 836 (M+H)$^+$ & 853 (M+NH4)$^+$

Example 17

Synthesis of Isopropanol Solvate of Cabazitaxel 220 g of 4α-acetoxy-2α-benzoyloxy-5β,20-epoxy-1β,13α-dihydroxy-7β,10β-dimethoxy-9-oxo-11-taxen-13α-yl-(2R,4S,5S)-3-tert-butoxycarbonyl-2-(4-methoxyphenyl)-4-phenyl-1,3-oxazolidine-5-carboxylate is dissolved in 3.3 L of methanol and 2.4 g of HCl. The solution is stirred for 6-7 h at 20-30° C. After the stirring 1.76 L of purified water is added slowly to the above solution and reaction mass is stirred for 1 h at 20-30° C. Again 2.64 L of purified water is slowly added to the reaction mixture and stirred for 1 h at 20-30° C. The solid is filtered and washed with highly purified water (HPW) (1.1 L×3). The wet cake is suck dried and treated with 1.2 L of iso-propanol. The reaction mass is stirred for 1 h at 20-30° C. and cooled to 0-10° C. The solid is filtered and washed with pre-cooled isopropanol (35 ml×2). The material is suck dried for 1 h. The solid material is dissolved in 308 ml of dichloromethane and stirred for 30 min at 20-30° C. 460 ml of isopropanol is slowly added to the reaction mixture and reaction mass is stirred for 30 min at 20-30° C. 1.85 L of IPA is again added slowly and stirred for 2 hours at 20-30° C. Reaction mass is cooled to 0 to 10° C. and stirred for 1 h at 0 to 10° C. The solid is filtered and washed with precooled iso-propanol (154×2) and suck dried for 2 h. the material is dried under vacuum for 6-8 h at 70-80° C. to get 152 g of IPA solvate of 4α-acetoxy-2α-benzoyloxy-5β,20-epoxy-1β,13α-dihydroxy-7β,10β-dimethoxy-9-oxo-11-taxen-13α-yl-(2R,4S,5S)-3-tert-butoxycarbonylamino-2-hydroxy-3-phenylpropionate.

Yield: 69%

Chromatographic Purity: 99.79%

DSC: 156.98° C.

TGA: 0.3494% w/w

PXRD angles 2-theta (Cu Kα radiation, λ=1.541 Å):: 7.3678, 7.8537, 8.9596, 10.2918, 12.5727, 12.8651, 13.3343, 13.5721, 14.4207, 14.7600, 15.1798, 15.3152, 15.6282, 15.7413, 16.5402, 16.9857, 17.6849, 17.9590, 18.3018, 18.6973, 18.7727, 19.4610, 20.4624, 20.6809, 21.1058, 21.1565, 21.4007, 21.7609, 21.9196, 22.2176, 23.1030, 23.5156, 23.7025, 24.2617, 24.7859, 25.1584, 25.8322, 26.3237, 27.0935, 27.4874, 27.7876, 28.3142, 28.9803, 30.1735, 30.6174, 31.2054, 31.5714, 32.2104, 32.3404, 32.9802±0.2

We claim:
1. A compound of Formula (XII)
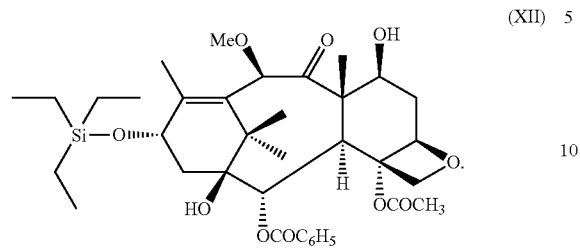
2. A compound of Formula (XIII)
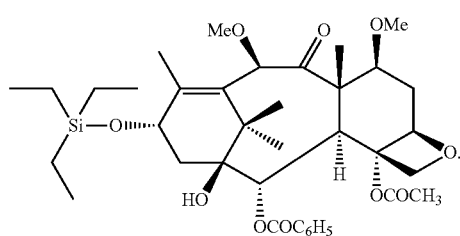
* * * * *